(12) United States Patent
Parks

(10) Patent No.: US 10,189,636 B2
(45) Date of Patent: Jan. 29, 2019

(54) INDICATOR SYSTEM FOR A COMBINED PROCEDURE DRAPE AND BAG

(71) Applicant: EndoChoice, Inc., Alpharetta, GA (US)

(72) Inventor: William Parks, Lawrenceville, GA (US)

(73) Assignee: EndoChoice, Inc., Alpharetta, GA (US)

(*) Notice: Subject to any disclaimer, the term of this patent is extended or adjusted under 35 U.S.C. 154(b) by 417 days.

(21) Appl. No.: 14/962,993

(22) Filed: Dec. 8, 2015

(65) Prior Publication Data

US 2016/0095665 A1     Apr. 7, 2016

Related U.S. Application Data

(62) Division of application No. 13/486,469, filed on Jun. 1, 2012, now Pat. No. 9,321,585.

(51) Int. Cl.
| | |
|---|---|
| B65D 33/00 | (2006.01) |
| B65D 33/28 | (2006.01) |
| B65D 85/00 | (2006.01) |
| B65B 7/00 | (2006.01) |
| A61B 46/00 | (2016.01) |
| A61B 50/36 | (2016.01) |

(Continued)

(52) U.S. Cl.
CPC .......... *B65D 85/70* (2013.01); *A61B 19/0287* (2013.01); *A61B 19/08* (2013.01); *A61B 46/00* (2016.02); *A61B 50/36* (2016.02); *A61B 90/90* (2016.02); *A61B 90/94* (2016.02); *A61B 90/96* (2016.02); *B65B 7/00* (2013.01); *A61B 2019/0226* (2013.01); *A61B 2019/0267* (2013.01); *A61B 2050/0071* (2016.02); *A61B 2050/314* (2016.02)

(58) Field of Classification Search
CPC .......... B65D 33/004; B65D 33/28; B65B 7/02
USPC ...................... 53/414; 383/61.4, 72
See application file for complete search history.

(56) References Cited

U.S. PATENT DOCUMENTS

| | | |
|---|---|---|
| 1,207,533 A | 12/1916 | Gamble |
| 3,475,767 A | 11/1969 | Friesen |

(Continued)

FOREIGN PATENT DOCUMENTS

CN          2329343 Y          7/1999

OTHER PUBLICATIONS

Office Action for CA2695800, dated May 1, 2017.

(Continued)

*Primary Examiner* — Gloria R Weeks
(74) *Attorney, Agent, or Firm* — Bookoff McAndrews, PLLC

(57) ABSTRACT

The present specification discloses a combined drape and carrying bag unit used in medical and surgical settings with an indicator attached to a drawstring of the unit. Conversion of the unit from a drape or mat configuration involves pulling on exposed drawstring sections and results in deployment of the identifying indicator. The indicator includes preprinted information, a barcode for scanning, and/or space for the inscription of information by medical personnel. The inclusion of an integrated indicator with the combined drape and carrying bag unit informs medical personnel of the contents of the unit when in the bag configuration and obviates the need for opening the bag and discovering its contents, thereby reducing exposure of medical personnel to biohazard waste.

9 Claims, 4 Drawing Sheets

(51) Int. Cl.
*A61B 90/90* (2016.01)
*A61B 90/96* (2016.01)
*A61B 19/02* (2006.01)
*A61B 19/08* (2006.01)
*A61B 90/94* (2016.01)
*A61B 50/30* (2016.01)
*A61B 50/00* (2016.01)

(56) References Cited

U.S. PATENT DOCUMENTS

| | | |
|---|---|---|
| 3,561,439 A | 2/1971 | Bayer |
| 3,650,267 A | 3/1972 | Anderson |
| 3,920,179 A | 11/1975 | Hall |
| 4,315,535 A | 2/1982 | Battle |
| 4,579,759 A | 4/1986 | Breuers |
| 4,608,283 A | 8/1986 | White |
| 4,738,545 A * | 4/1988 | Westgor ............... A45C 9/00 190/1 |
| 4,800,677 A | 1/1989 | Mack |
| 4,813,792 A | 3/1989 | Belmont |
| 4,923,453 A | 5/1990 | Bullard |
| 4,931,052 A | 6/1990 | Feldman |
| 4,975,688 A * | 12/1990 | Gonzales ............... G08B 17/10 150/165 |
| 4,991,978 A | 2/1991 | Ostrowski |
| 5,078,508 A | 1/1992 | Johan |
| 5,092,681 A | 3/1992 | Ashley, III |
| 5,151,314 A | 9/1992 | Brown |
| 5,291,999 A | 3/1994 | Phair |
| 5,319,162 A | 6/1994 | Ness |
| 5,388,743 A | 2/1995 | Silagy |
| 5,416,279 A | 5/1995 | Tseng |
| 5,417,462 A | 5/1995 | Hensley |
| 5,456,062 A | 10/1995 | Wechsler |
| 5,464,024 A * | 11/1995 | Mills .................... A61B 46/00 128/849 |
| 5,476,456 A | 12/1995 | Rankin |
| 5,716,137 A | 2/1998 | Meyer |
| 5,816,253 A | 10/1998 | Sosebee |
| D410,574 S | 6/1999 | McCaig |
| 5,988,172 A | 11/1999 | Sosebee |
| 6,270,821 B1 | 8/2001 | Grip |
| 6,282,725 B1 | 9/2001 | Vanidestine, Jr. |
| 6,651,362 B2 | 11/2003 | Caveney |
| 6,777,044 B1 | 8/2004 | Jeandemange |
| 6,976,451 B2 | 12/2005 | Helfman |
| 7,096,870 B2 | 8/2006 | Lamprich |
| 7,313,894 B2 * | 1/2008 | Mise .................... B65B 11/54 156/560 |
| 7,543,587 B2 | 6/2009 | Yardan |
| 7,594,754 B2 | 9/2009 | Costello |
| 8,042,688 B2 * | 10/2011 | Parks .................. A45C 9/00 128/849 |
| 8,454,236 B2 | 6/2013 | Ramirez |
| 8,544,922 B1 | 10/2013 | Huzar |
| 9,084,459 B2 | 7/2015 | Fazackerley |
| 2004/0016654 A1 | 1/2004 | Franzen |
| 2006/0191540 A1 | 8/2006 | Lamprich |
| 2007/0084866 A1 | 4/2007 | Saeugling |

OTHER PUBLICATIONS

International Search Report for International Application No. PCT/US2008/074395 dated Oct. 31, 2008.
Office Action dated Feb. 3, 2015 for U.S. Appl. No. 13/486,469.
Office Action dated Jun. 8, 2015 for U.S. Appl. No. 13/486,469.
First Office Action for CN20120058948.3, dated Jan. 3, 2014.
Notice of Allowance dated Dec. 21, 2015 for U.S. Appl. No. 13/486,469.
First office action for CA2695800, dated Apr. 14, 2015.

\* cited by examiner

INDICATOR SYSTEM FOR A COMBINED PROCEDURE DRAPE AND BAG

CROSS-REFERENCE

The present specification is a divisional application of U.S. patent application Ser. No. 13/486,469, filed on Jun. 1, 2012, of the same title, which also corresponds to United States Patent Publication Number 20130318927.

FIELD

The present specification relates generally to disposable pads and bags used in medical and surgical procedures for placement under both the patient and instruments and for the disposal of waste materials. More particularly, the present specification relates to an indicator integrated into a combined procedure drape and carrying bag unit.

BACKGROUND

Conventional disposable absorbent drapes or pads used in medical and surgical procedures are often comprised of a plurality of absorbent and impermeable material layers joined mechanically to produce a sterile mat of given geometry. These mats are placed upon medical carts to establish a sterile work platform upon which surgical, endoscopic and other medical instruments may be placed upon, beneath the patient procedure zone, to contain wastes emanating from the procedure due to gravitational flow from the patient's body, and on other such areas in the procedural region to allow for capture of waste or the establishment of a sterile work surface.

With regards to a conventional absorbent drape, once the procedure is complete, the equipment involved in the procedure, which is now contaminated, is removed from the area by medical personnel. The equipment may be placed in a separate container for transport or left exposed to the environment and carried to a decontamination/sterilization area for preparation in the next procedural use. The absorbent disposable drapes used in the procedure are gathered by medical personnel and placed in containers or receptacles for proper disposal of biohazard materials.

During removal of the equipment and drapes, medical personnel may be exposed to biohazard materials deposited on the equipment and drapes. Procedures are commonly employed to reduce the level of exposure, but movement or disposal of the equipment and drapes still involves the placement of the affected articles into separate containers and transport or disposal units, and still involves exposure of medical personnel to biohazard materials deposited thereon. A combined drape and carrying bag unit has been described in U.S. Pat. No. 8,042,688, assigned to the applicant of the present invention, to limit medical personnel exposure to waste materials, collect all used equipment, and eliminate the need for a separate container, and is hereby incorporated by reference in its entirety.

What is additionally needed in, and beneficial to, drape and carrying bag units is a means of informing medical personnel of the contents of the bag once it has been closed, without the need of re-opening or looking inside the bag. Therefore, what is needed is an integrated labeling or identifying means that would become visible only after the procedure has been completed and the drape and carrying bag unit has been changed to its carrying bag configuration. Such an identifying means would inform medical personnel if the bag contains biohazard waste, used medical and/or surgical instruments, or some other post-procedural byproduct.

SUMMARY

The present specification is directed toward a device for identifying contents of a combined drape and carrying bag unit used in medical and surgical settings. In one embodiment, the specification discloses a device for identifying contents of a combined drape and carrying bag unit, comprising a drawstring contained within a drawstring casing, for use in medical and surgical settings, comprising an indicator fixedly attached to a portion of said drawstring, wherein said indicator is compressed and hidden in the drawstring casing while said unit is in a first, mat configuration and said indicator is deployed and exposed outside the drawstring casing when said unit is converted into a second, carrying bag configuration.

Optionally, the indicator is sewn to the drawstring. The indicator comprises at least one of a flag, label, tag, card, rectangle, square, circle, or oval. The indicator is rectangular in shape and measures between 3 and 6 inches in length by 2 and 4 inches in width. The unit is converted from the first, mat configuration into the second, carrying bag configuration by pulling the drawstring through at least one space in the drawstring casing. When the unit is in the first, mat configuration, the indicator is positioned along the drawstring approximately 20-60 cm from the at least one space. When the unit is in the first, mat configuration, the indicator is positioned along the drawstring approximately 40 cm from the at least one space. The indicator contains preprinted information, a barcode for scanning, space for inscription of information by medical personnel, or any combination of the above.

In another embodiment, the present specification discloses a system for identifying contents of a combined drape and carrying bag unit used in medical and surgical settings, comprising a combined drape and bag carrying unit convertible from a first, mat configuration to a second, carrying bag configuration, said unit comprising a centrally positioned, generally rectangular shaped portion for receiving an instrument, a drawstring casing along the periphery of said unit with a continuous drawstring disposed therein, and at least two drawstring access openings positioned along said drawstring casing, thereby exposing a portion of said drawstring to medical personnel and an indicator fixedly attached to said drawstring along a particular length of said drawstring, said indicator is contained within said drawstring casing while said combined drape and bag carrying unit is in said first configuration, such that conversion of said unit from said first configuration to said second configuration results in said indicator automatically becoming deployed and exposed from said drawstring casing through at least one of said drawstring access openings.

Optionally, the indicator is attached to said drawstring at a position between 20 and 60 cm along the drawstring from at least one of said drawstring access openings when said unit is in said first configuration. The indicator is attached to said drawstring at a position 40 cm along the drawstring from at least one of said drawstring access openings when said unit is in said first configuration. The indicator is sewn to the drawstring. The indicator comprises at least one of a flag, label, tag, card, rectangle, square, circle, or oval. The indicator is rectangular in shape and measures between 3 and 6 inches in length by 2 and 4 inches in width.

In another embodiment, the present specification discloses a device for identifying contents of a combined drape and carrying bag unit, comprising a drawstring contained within a drawstring casing, for use in medical and surgical settings, comprising a first indicator portion of said drawstring and a second portion of said drawstring, wherein said first indicator portion visually differentiates said first indicator portion from the second portion of the drawstring, wherein said first indicator portion is hidden in the drawstring casing while said unit is in a first, mat configuration and wherein said first indicator portion is deployed and exposed outside the drawstring casing when said unit is converted into a second, carrying bag configuration.

Optionally, the first indicator portion comprises a portion of the drawstring that is a different color from the second portion of the drawstring. The unit is converted from the first, mat configuration into the second, carrying bag configuration by pulling the drawstring through at least one space in the drawstring casing. When the unit is in the first, mat configuration, the first indicator portion is positioned along the drawstring approximately 20-60 cm from the at least one space. When the unit is in the first, mat configuration, the first indicator portion is positioned along the drawstring approximately 40 cm from the at least one space.

In another embodiment, the present specification discloses a method for deploying an indicator integrated with a combined drape and carrying bag unit used in medical and surgical settings, comprising laying out a combined drape and bag carrying unit convertible from a first, mat configuration to a second, carrying bag configuration, said unit comprising: a centrally positioned, generally rectangular shaped portion for the disposition of an instrument, a drawstring casing along the periphery of said unit with a continuous drawstring disposed therein, at least two drawstring access openings positioned along said drawstring casing, thereby exposing a portion of said drawstring to medical personnel, and an indicator fixedly attached to said drawstring along a particular length of said drawstring, said indicator contained within said drawstring casing while said combined drape and bag carrying unit is in said first configuration; and placing medical waste or used medical equipment in the centrally positioned, generally rectangular shaped portion; and pulling on portions of said drawstring exposed at said drawstring access openings, thereby converting said unit from said first configuration to said second configuration by gathering together said periphery of said unit and forming a bag and further thereby deploying and exposing said indicator by pulling said particular length of drawstring with attached indicator out of said drawstring casing.

These, and other embodiments, shall be further described in the Detailed Description in relation to the drawings.

BRIEF DESCRIPTION OF THE DRAWINGS

These and other features and advantages of the present invention will be further appreciated, as they become better understood by reference to the detailed description when considered in connection with the accompanying drawings.

DETAILED DESCRIPTION

Figure 1:
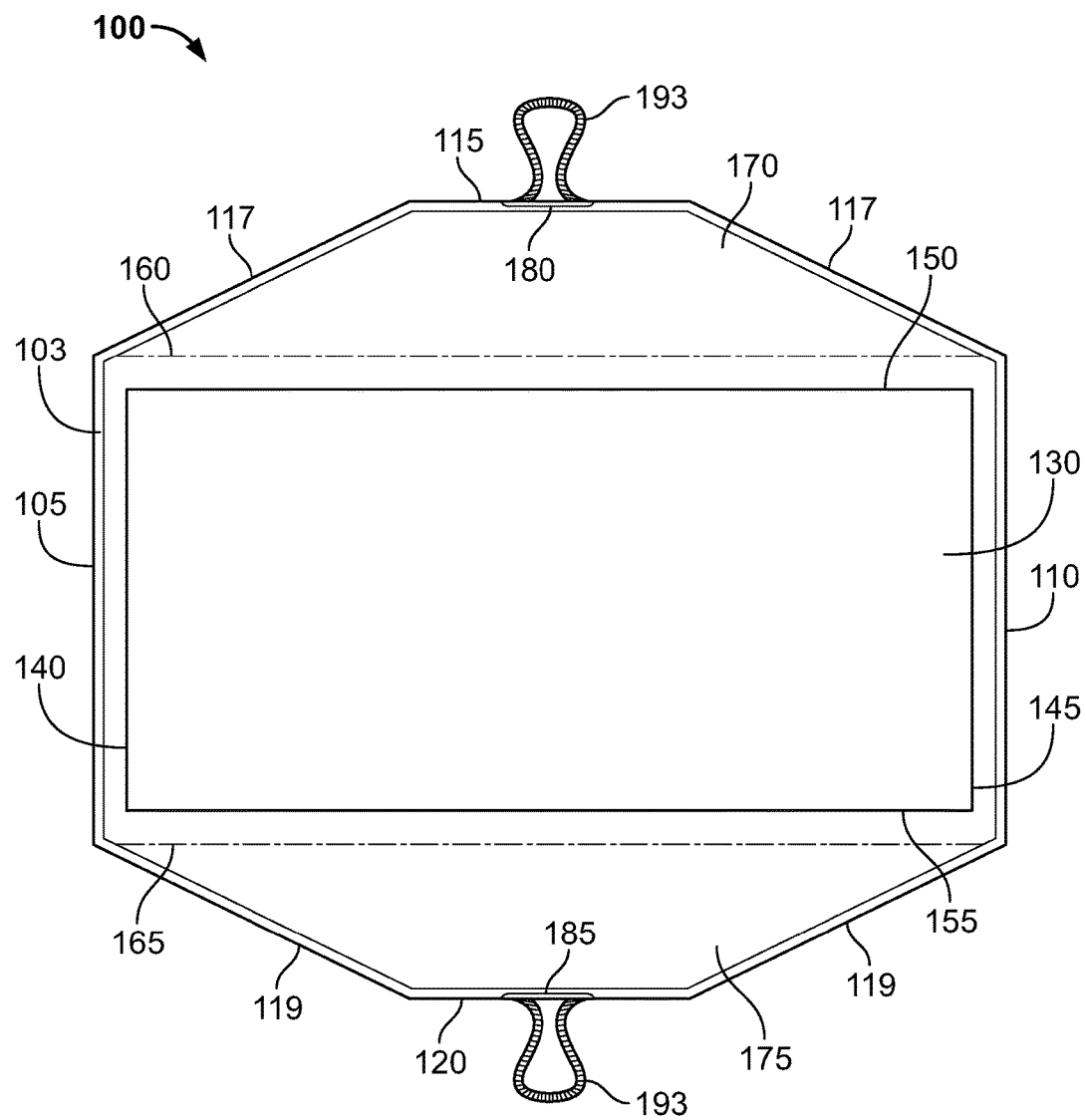
FIG. 1 is a top-down illustration of an exemplary embodiment of a drape and carrying bag unit in the mat configuration, to be used with the indicator of the present specification.

The present specification is directed toward an indicator to be used in combination with a combined drape and carrying bag unit, said unit for use as a sterile or non-sterile surface mat during medical and surgical procedures and conversion of same through operation of embodied features therein to a carrying bag for the containment of procedural equipment and post-procedural waste.

In one embodiment, the indicator is integrated with the drape and carrying bag unit and hidden while the unit is in the drape configuration and exposed once the unit is converted to the carrying bag configuration. In various embodiments, the indicator comprises a flag, label, tag, or card with space available for alphanumeric and/or barcode information. As would be clear to one experienced in the art, in other embodiments, the indicator could take any other form or shape not listed above that would be easy for medical personnel to locate and read. In one embodiment, the indicator has preprinted information thereupon. In another embodiment, the indicator is blank and allows for inscription of identifying information by medical personnel. In yet another embodiment, the indicator includes both preprinted information and space for the inscription of additional information. The information included on the indicator informs medical personnel of the contents of the unit when in the carrying bag configuration, obviating the need for medical personnel to re-open the bag and visually inspect the contents, thereby limiting exposure to biohazard waste.

As described in U.S. Pat. No. 8,042,688, which is incorporated herein by reference in its entirety, the drape and carrying bag unit comprises a singular sheet or plurality of joined or attached sheets of pliable materials, both permeable and impermeable, of a size to define a mat to accommodate a working medical procedural area thereon, upon which may be placed in single or combination, medical equipment and biomaterials extracted from a patient. In one embodiment, the mat is of size to accommodate a patient's procedural volume thereon. In various embodiments, the mat is also suitable for use as a sterile or non-sterile procedural mat, medical cart mat, prep area mat, or the like. A drawstring casing extends about the periphery of the drape and has a plurality of openings therein. A drawstring is received in the drawstring casing and is of size to extend about the periphery of the drape when it defines a mat. The drawstring is slidably received in the drawstring casing so that when portions of the drawstring are pulled out of the drawstring casing through the openings, the periphery of the drape forms gathers adjacent the casing to permit the periphery to reduce in size and form a carrying bag.

In one embodiment, the drape has a generally rectangular periphery defined by two generally parallel side edges and two generally parallel end edges, the side edges being longer than and generally perpendicular to the end edges. The drawstring casing includes, but is not limited to, two openings positioned proximate the midpoints of those portions of the casing which extend along the end edges.

When portions of the drawstring are pulled out of the two openings and such drawstring portions are secured together adjacent the openings, a handle portion is formed. The handle portion is comprised of the drawstring casing, those portions of the drape adjacent the drawstring casing and those portions of the drawstring pulled out of the openings. In one embodiment, the indicator of the present specification is fixedly connected to the drawstring. The indicator is affixed to a specific segment of the drawstring such that, when the drape and carrying bag unit is in its drape or mat configuration, the indicator is positioned within the drawstring casing and is not visible. In another embodiment, the indicator is in the form of a differently colored portion of the drawstring itself, including a differently colored portion of the drawstring, a highlighted portion of the drawstring, a printed on portion of the drawstring, or some otherwise physically modified portion of the drawstring to create the desired indicator.

When a medical professional pulls on the drawstrings at the openings and the unit converts to the carrying bag configuration, the section of drawstring with the indicator attached becomes exposed and the indicator is deployed. In one embodiment, the indicator is folded or rolled to minimize area and unfolds or unfurls once it comes out of the drawstring casing. The present invention is directed toward multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

FIG. 1 is a top-down illustration of an exemplary embodiment of a drape and carrying bag unit 100 in the mat configuration, to be used with the indicator of the president specification. In the pictured embodiment, the drape and carrying bag unit 100 has an elongated octagonal shape with opposing straight end edges 105, 110, opposing straight side edges 115, 120, and angled corner edges 117, 119. In one embodiment, the opposing straight side edges 115, 120 are longer than the opposing straight end edges 105, 110. In one embodiment, opposing straight side edges 115, 120 are parallel to each other and opposing straight end edges 105, 110 are parallel to one another, with the opposing side edges 115, 120 generally perpendicular to the opposing straight end edges 105, 110. In addition, in various embodiments, angled corner edges 117, 119 are arranged at any angle less than 180° with respect to end edges 105, 110 and with respect to side edges 115, 120. In various embodiments, the angled corner edges are arranged at smaller angles with respect to the end edges 105, 110 than to the side edges 115, 120. In other embodiments, the angled corner edges are arranged at larger angles with respect to the end edges 105, 110 than to the side edges 115, 120. In one embodiment, angled corner edges 117, 119 are arranged at the same angle with respect to the end edges 105, 110 as to the side edges 115, 120.

In one embodiment, a centrally located absorbent mat 130 is embedded within the unit 100, having a generally rectangular shape defined by two generally parallel end edges 140, 145 and two generally parallel side edges 150, 155. The unit also includes two creases 160, 165, about which draping sections 170, 175 are folded and hang down from the sides of a procedure table.

A drawstring casing or annulus 103 extends around the periphery of the drape and carrying bag unit 100. A continuous drawstring 193 is positioned within the drawstring casing 103. In one embodiment, two drawstring access openings 180, 185 or are positioned proximate the center of each side edge 115, 120. In another embodiment (not shown), the drawstring access openings are positioned proximate the center of each end edge. A portion of drawstring 193 is exposed and accessible to medical personnel at each of these two openings 180, 185. Simultaneously pulling on each exposed portion of drawstring 193 causes the side edges 115, 120, end edges 105, 110, and angled corner edges 117, 119 to be drawn and cinched together, resulting in a change in shape of the unit 100 from the drape or mat configuration to the carrying bag configuration. Any instruments, biohazard waste, or other objects lying on the unit at the time of cinching become enclosed within the carrying bag for transfer or disposal.

Figure 2:
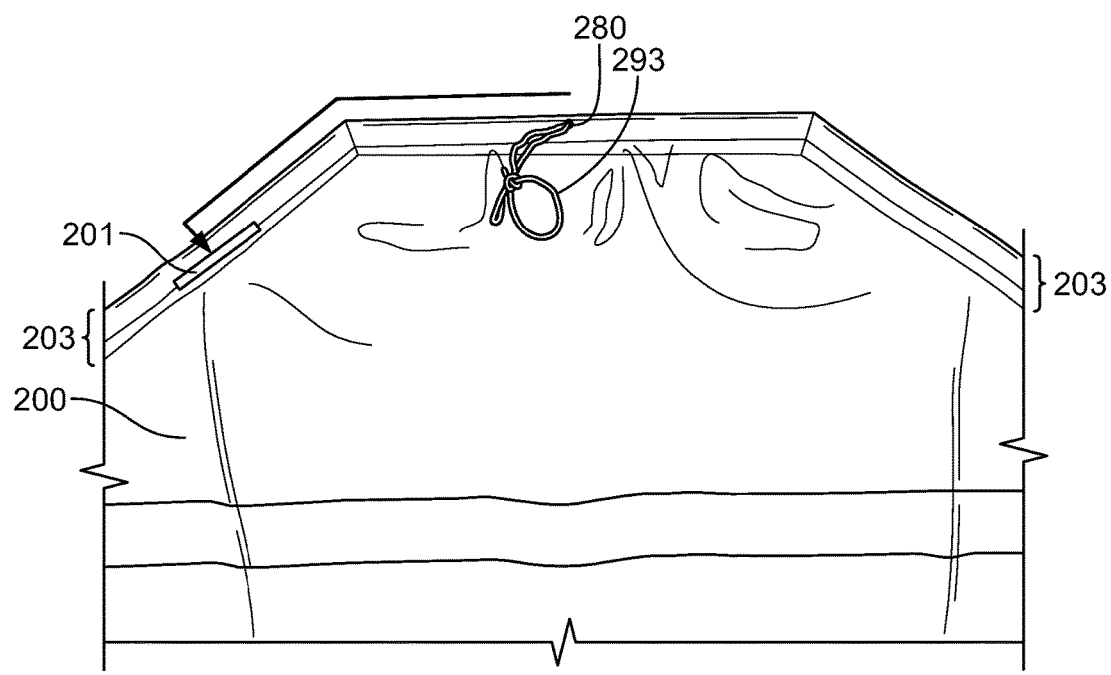
FIG. 2 is a close-up view illustration of one end of a drape and carrying bag unit, depicting a segment of drawstring exposed at a drawstring access opening and the positioning of an indicator within the drawstring casing, in accordance with one embodiment of the present specification.

In one embodiment, an indicator is fixedly attached to a portion of the drawstring proximate one of the drawstring access openings. The indicator and drawstring are slidably movable within the drawstring casing. As the drawstring is pulled, the attached indicator will be pulled along with it. FIG. 2 is a close-up view illustration of one end of a drape and carrying bag unit 200, depicting a segment of drawstring 293 exposed at a drawstring access opening 280 and the positioning 201 of an indicator within the drawstring casing 203, in accordance with one embodiment of the present specification. Referring to FIG. 2, the drape and carrying bag unit 200 is in the mat configuration; hence the indicator is still positioned within the drawstring casing 203 and is not visible. The relative position 201 of the indicator has been marked to assist in visualization. In one embodiment, the indicator is sewn to the drawstring. In various embodiments, the indicator is attached to the drawstring at a point between 20 and 60 cm along the drawstring from the appropriate drawstring access opening, when the drape and carrying bag unit is in the mat configuration. In one embodiment, the indicator is attached to the drawstring at a point 20-60 cm (including all integer and fractional increments therein), and preferably 40 cm, along the drawstring from the appropriate drawstring access opening, when the drape and carrying bag unit is in the mat configuration.

In one embodiment, the indicator is folded or rolled to minimize its size and more easily fit within the drawstring casing 203. As the drawstring 293 is pulled, the indicator pulls along with it and exits the drawstring casing 203 at the drawstring access opening 280, becoming fully deployed. Deployment involves unfolding, decompressing, or unfurling of the indicator.

Figure 3:
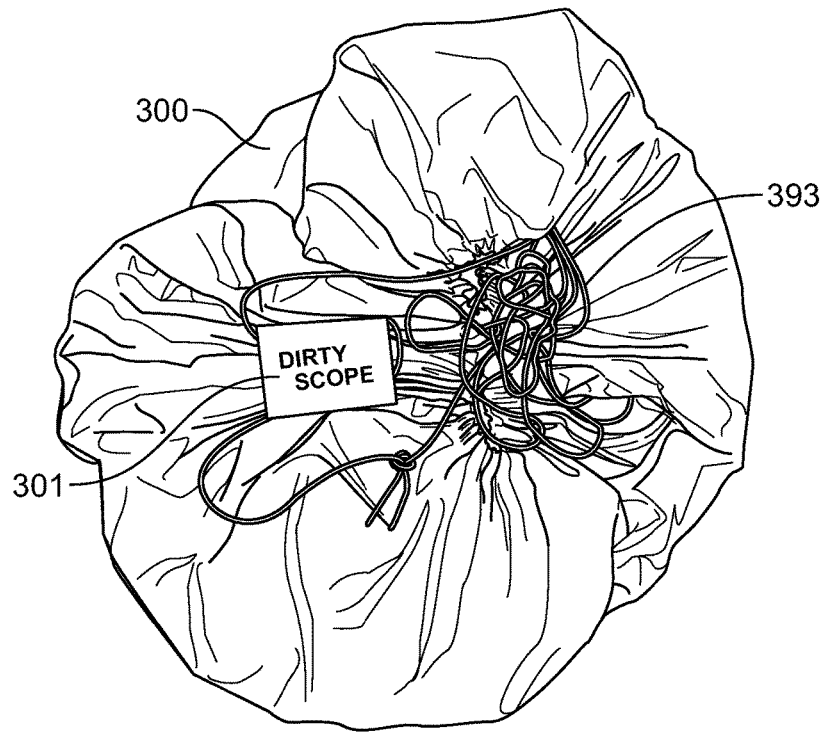
FIG. 3 is a top-down illustration of an exemplary embodiment of a drape and carrying bag unit in the bag configuration, depicting the indicator deployed and attached to the drawstring.

FIG. 3 is a top-down illustration of an exemplary embodiment of a drape and carrying bag unit 300 in the bag configuration, depicting the indicator 301 deployed and attached to the drawstring 393. In various embodiments, the indicator 300 is a flag, label, tag, card, or other easily recognizable item known to persons experienced in the art.

In one embodiment, the indicator is in the shape of a rectangle, square, circle, oval, or any other shape easily recognizable and foldable for storing in said drawstring casing. In one embodiment, the indicator is rectangular in shape and measures between 3 and 6 inches in length by 2 and 4 inches in width. In addition, in one embodiment, the indicator is composed of a material that facilitates passive unfolding or unfurling once deployed and may comprise nylon, silk, cotton, polyester, polypropylene, and/or biodegradable polymers. In one embodiment, the indicator is colored red to enhance visualization. In other embodiments, the indicator is of a different color to help differentiate it from the carrying bag. In one embodiment, the indicator includes preprinted alphanumeric information to inform medical personnel of the contents of the bag. In one embodiment, the indicator reads "Dirty Scope". In another embodiment, the indicator includes a barcode for scanning. In another embodiment, the indicator includes a blank space for the inscription of information by medical personnel. In various embodiments, the indicator includes any combination of preprinted text, barcode, and/or blank space.

Figure 4:
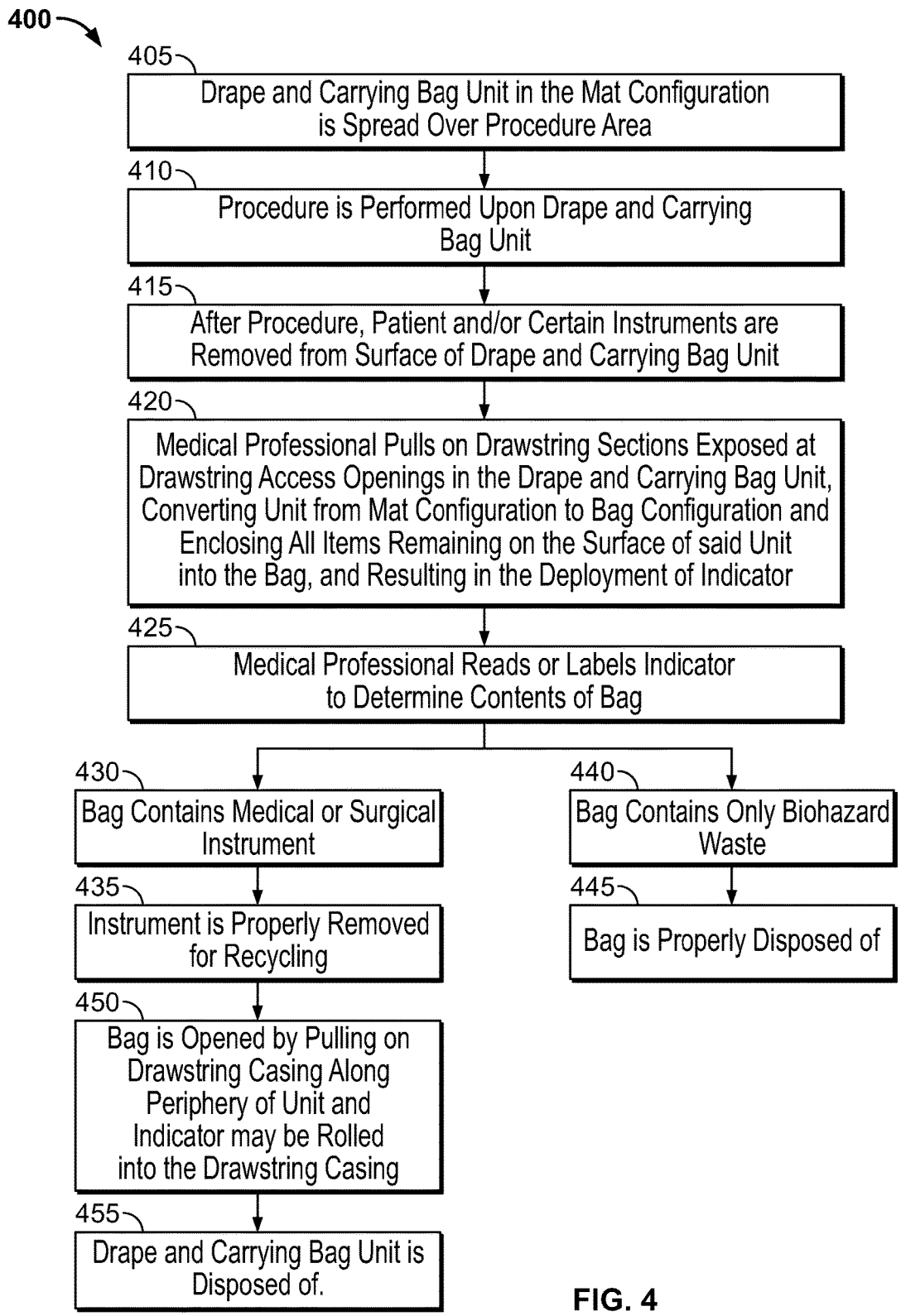
FIG. 4 is a flowchart illustrating an exemplary embodiment of the steps involved in the deployment and use of the indicator of the present specification.

FIG. 4 is a flowchart 400 illustrating an exemplary embodiment of the steps involved in the deployment and use of the indicator of the present specification. At step 405 a drape and carrying bag unit in the mat configuration is spread over procedure area. A medical or surgical procedure is then performed upon the drape and carrying bag unit at step 410. After the procedure, at step 415, the patient and/or certain instruments are removed from surface of drape and carrying bag unit. At step 420, a medical professional pulls on the drawstring sections exposed at the two drawstring access openings on opposite sides of the drape and carrying bag unit, converting the unit from the mat configuration to the bag configuration and enclosing all items remaining on the surface of the unit inside the bag, and also resulting in the deployment of indicator.

At step 425, a medical professional reads or labels indicator to determine contents of bag. In one embodiment, the medical professional scans a barcode on the indicator to determine and log the contents of the bag. If the bag contains medical or surgical instrument as in step 430, the instrument is properly removed for recycling at step 435. In one embodiment, recycling of the instrument(s) includes cleaning, sterilizing, and repackaging/labeling of the instrument for future use. Once the instrument has been removed, or, if the bag initially did not contain any instruments, the bag only contains biohazard waste as in step 440.

In one embodiment, the bag containing only biohazard waste is properly disposed of in step 445. In another embodiment, in step 450, the bag is opened, allowing drawstring and indicator to feed back into the drawstring casing, and the medical equipment is accessed and then properly cleaned, sterilized, and packaged for repeat use. The drape and carrying bag unit is disposed of 455.

It should be appreciated that, while the drape and carrying bag is shown as an octagonal shape, it can be of any shape that includes a central mat area with side portions extending therefrom and that is configured to adopt a bag shape upon constriction of a drawstring extending around the periphery of the central mat and side portions.

Figure 5:
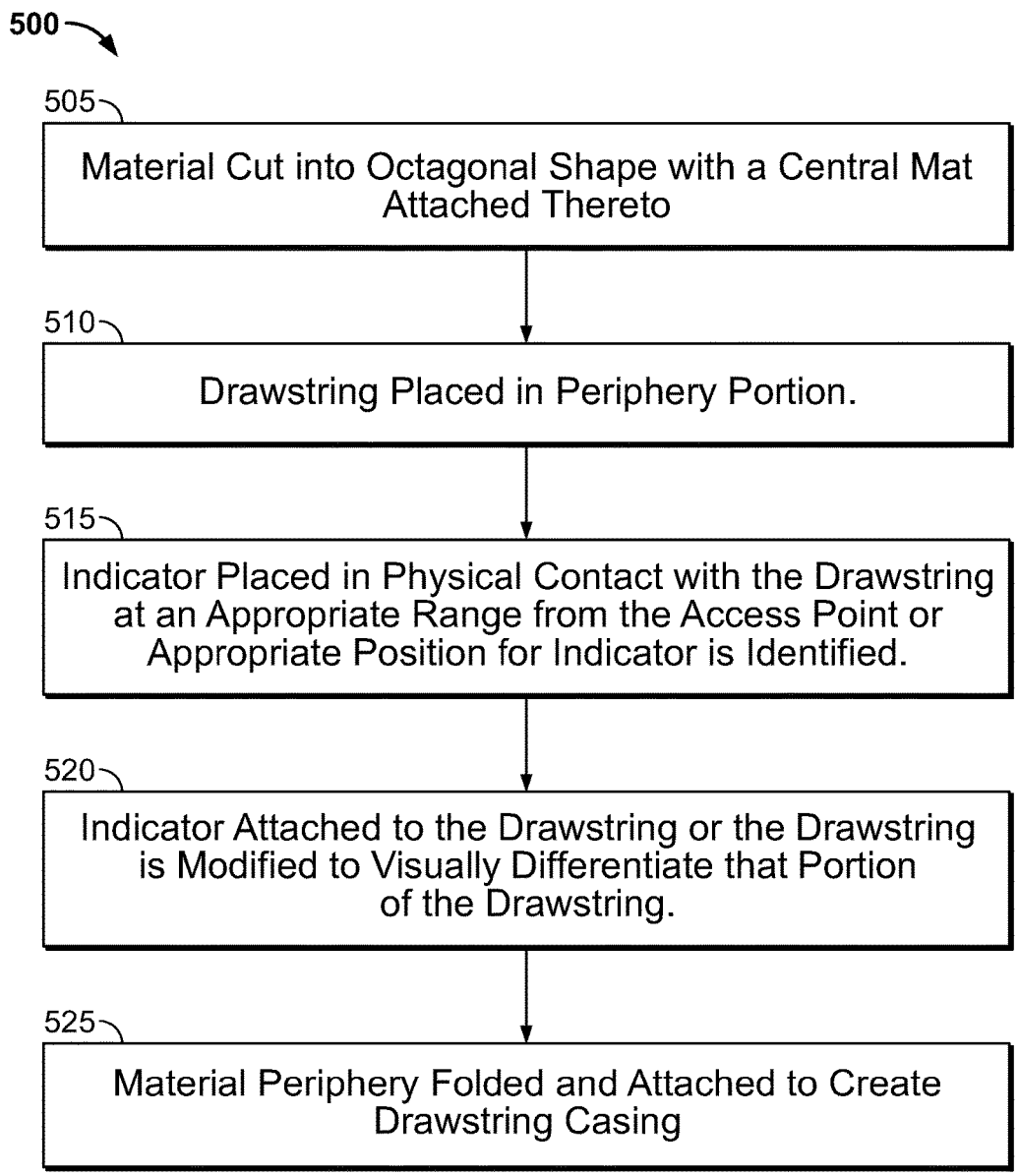
FIG. 5 is a flowchart illustrating an exemplary method of manufacturing a drape and carrying bag unit with an indicator.

FIG. 5 is a flowchart depicting one process 500 for manufacturing the drape and carrying bag with integrated indicator. After a material is cut into the octagonal shape shown in FIG. 1 with a central mat attached thereto 505, a drawstring is placed 510 in the material's edge portion, which, during this stage of the manufacturing process, is planar and unfolded. The drawstring is of sufficient length to extend around the entire periphery of the material and form accessible loops through the two access points.

An indicator is then attached to the drawstring by placing 515 the indicator, such as a flag or tag, in physical contact with a portion of the drawstring at a location that is sufficiently close to the access point such that, upon pulling the drawstring through the access point, it causes the indicator to be pulled out of the drawstring casing through the access point but not so close as to be visible to a user when the drape and carrying bag is in a mat, or flat, configuration. In one embodiment, the indicator is placed at a point that is 20-60 cm (including all integer and fractional increments therein), and preferably 40 cm, along the drawstring from a drawstring access opening, when the drape and carrying bag unit is in the mat configuration.

After the indicator is placed in the appropriate physical location 515, the indicator is attached to the drawstring 520. The indicator may be attached to the drawstring by folding the indicator around the drawstring and attaching to the indicator to itself, sewing the indicator to the drawstring or to itself (which is wrapped around the drawstring), ultrasonic welding the indicator to the drawstring or to itself (which is wrapped around the drawstring), chemically adhering the indicator to the drawstring or to itself (which is wrapped around the drawstring), thermal/melting the indicator to the drawstring or to itself (which is wrapped around the drawstring), or heat tubing the indicator to the drawstring or to itself (which is wrapped around the drawstring).

After the indicator is attached 515, the edges of the material are folded over the drawstring, and the edges are attached to the body of the material, to thereby create a drawstring casing 525. In one embodiment, to minimize the likelihood of the indicator being improperly sewn to the material in the process of creating the drawstring casing, the edges of the drawstring casing may be attached and, before attaching the portion of the drawstring casing where the indicator and drawstring reside, the indicator and drawstring may be temporarily repositioned while the drawstring casing is formed. Once formed, the indicator and drawstring are then repositioned into the appropriate location. In one embodiment, the drawstring casing if formed by sewing, ultrasonic welding, chemical adherence, thermal/melting, or heat tubing.

Where the indicator is in the form of a differently colored portion of the drawstring itself, after the drawstring is placed in the appropriate position 510, an appropriate location for the indicator is identified 515 and the drawstring is colored, highlighted, printed on, or otherwise physically modified to create the desired indicator 520.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. A method for deploying an indicator integrated with a combined drape and carrying bag unit used in medical and surgical settings, comprising:

laying out a combined drape and bag carrying unit convertible from a first, mat configuration to a second, carrying bag configuration, said unit comprising:

a centrally positioned, generally rectangular shaped portion for the disposition of an instrument, a drawstring casing along the periphery of said unit with a continuous drawstring disposed therein, at least two drawstring access openings positioned along said drawstring casing, thereby exposing a portion of said drawstring to medical personnel, and an indicator fixedly attached to said drawstring along a particular length of said drawstring, said indicator contained within said drawstring casing while said combined drape and bag carrying unit is in said first configuration; and placing medical waste or used medical equipment in the centrally positioned, generally rectangular shaped portion;

pulling on portions of said drawstring exposed at said drawstring access openings, thereby converting said unit from said first configuration to said second configuration by gathering together said periphery of said unit and forming a bag and further thereby deploying and exposing said indicator by pulling said particular length of drawstring with attached indicator out of said drawstring casing; and writing on the indicator after the indicator is deployed.

2. The method of claim 1, wherein the indicator unfolds or unfurls when deployed.

3. The method of claim 1, wherein the indicator expands outwardly from the drawstring when deployed.

4. The method of claim 1, wherein the indicator is sewn to the drawstring.

5. A method for deploying an indicator integrated with a combined drape and carrying bag unit, the method comprising:

laying out the combined drape and carrying bag unit in a mat configuration, wherein the unit is convertible from the mat configuration to a carrying bag configuration, the unit comprising:

a centrally positioned portion, a drawstring casing along the periphery of the unit, a drawstring disposed within the drawstring casing, a first drawstring access opening positioned along the drawstring casing, wherein the first drawstring access opening is configured to expose a first U-shaped portion of the drawstring from the drawstring casing, a second drawstring access opening positioned along the drawstring casing, wherein the second drawstring access opening is configured to expose a second U-shaped portion of the drawstring from the drawstring casing, and an indicator fixedly attached to the drawstring, said indicator being contained within the drawstring casing while the combined drape and bag carrying unit is in the mat configuration;

placing medical waste or used medical equipment on the centrally positioned portion;

pulling the first U-shaped portion of the drawstring to withdraw the indicator from the drawstring casing via the first drawstring access opening, thereby exposing the indicator, wherein the indicator is coupled to the first U-shaped portion of the drawstring when exposed; and writing on the indicator after the indicator is exposed.

6. The method of claim 5, wherein the indicator transitions from a folded state to an unfolded state when the indicator is exposed.

7. The method of claim 5, wherein the indicator transitions from a rolled state to an unrolled state when the indicator is exposed.

8. The method of claim 5, wherein the indicator includes a barcode for scanning.

9. The method of claim 5, wherein pulling the first U-shaped portion of the drawstring initially causes the indicator to slide through the drawstring casing without exposing the indicator.

* * * * *